United States Patent
Abram et al.

(10) Patent No.: US 9,827,195 B2
(45) Date of Patent: **\*Nov. 28, 2017**

(54) FATTY ACID PHARMACEUTICAL FOAM

(71) Applicant: STIEFEL RESEARCH AUSTRALIA PTY LTD, Rowville, Victoria (AU)

(72) Inventors: Albert Zorko Abram, Wantirna (AU); Iulian Goldstein, Ferntree Gully (AU)

(73) Assignee: STIEFEL RESEARCH AUSTRALIA PTY LTD, Rowville, Victoria (AU)

( * ) Notice: Subject to any disclaimer, the term of this patent is extended or adjusted under 35 U.S.C. 154(b) by 27 days.

This patent is subject to a terminal disclaimer.

(21) Appl. No.: 14/683,672

(22) Filed: Apr. 10, 2015

(65) Prior Publication Data

US 2015/0209280 A1    Jul. 30, 2015

Related U.S. Application Data

(63) Continuation of application No. 11/826,199, filed on Jul. 12, 2007, now Pat. No. 9,023,863.

(60) Provisional application No. 60/830,949, filed on Jul. 14, 2006.

(51) Int. Cl.
| | | |
|---|---|---|
| A61K 31/437 | (2006.01) | |
| A61K 9/12 | (2006.01) | |
| A61K 9/00 | (2006.01) | |
| A61K 47/14 | (2017.01) | |
| A61K 31/4745 | (2006.01) | |
| A61K 47/12 | (2006.01) | |
| A61K 47/18 | (2017.01) | |

(52) U.S. Cl.
CPC ............ *A61K 9/122* (2013.01); *A61K 9/0014* (2013.01); *A61K 9/124* (2013.01); *A61K 31/437* (2013.01); *A61K 31/4745* (2013.01); *A61K 47/12* (2013.01); *A61K 47/14* (2013.01); *A61K 47/18* (2013.01); *A61K 9/12* (2013.01)

(58) Field of Classification Search
None
See application file for complete search history.

(56) References Cited

U.S. PATENT DOCUMENTS

| | | | |
|---|---|---|---|
| 4,689,338 A | 8/1987 | Gerster | |
| 5,238,944 A | 8/1993 | Wick et al. | |
| 5,589,515 A | 12/1996 | Suzuki et al. | |
| 5,700,396 A | 12/1997 | Suzuki et al. | |
| 5,736,553 A | 4/1998 | Wick et al. | |
| 5,993,830 A | 11/1999 | Freij | |
| 6,706,728 B2 | 3/2004 | Hendenstrom et al. | |
| 7,186,416 B2 | 3/2007 | Popp et al. | |
| 2002/0001599 A1 | 1/2002 | Neubourg | |
| 2002/0016332 A1 | 2/2002 | Slade | |
| 2003/0161797 A1 | 8/2003 | Miller et al. | |
| 2003/0199538 A1 | 10/2003 | Skwierczynski et al. | |
| 2004/0180919 A1 | 9/2004 | Miller et al. | |
| 2005/0079139 A1 | 4/2005 | Jacques et al. | |
| 2005/0222090 A1 | 10/2005 | Cheng et al. | |

FOREIGN PATENT DOCUMENTS

| | | |
|---|---|---|
| EP | 0233629 B1 | 10/1991 |
| EP | 0376534 B1 | 12/1993 |
| GB | 1 397 285 A | 6/1975 |
| WO | 2004/037225 A2 | 5/2004 |
| WO | 2006003481 A2 | 1/2006 |

OTHER PUBLICATIONS

Supplementary European Search Report, dated Sep. 22, 2010, 13 pages.
Third party opposition filed in counterpart published Argentine Application No. P070103126 by Roemmers S.A.I.C.F. on Jan. 15, 2009, (with full translation).
Third part opposition filed in counterpart published Argentine Application No. P070103126 by Atlas Farmaceutica S.A. on Dec. 30, 2008, (with full translation).

*Primary Examiner* — James D Anderson
*Assistant Examiner* — Meghan Finn
(74) *Attorney, Agent, or Firm* — Nath, Goldberg & Meyer; Joshua B. Goldberg; Scott H. Blackman

(57) ABSTRACT

The present invention provides a foamable composition comprising water and an organic solvent, wherein the organic solvent comprises a fatty acid. The composition may further comprise a pharmaceutically active agent. The composition of the invention is also useful for the treatment of a dermatological disorder in a mammal by the topical administration of the composition.

20 Claims, 3 Drawing Sheets

Table 3 - Foam Stability - Appearance & Static Stability (at Room Temperature ~ 20 °C)

| Batch # | 645-07-01 | 645-07-02 | 645-07-03 | 645-07-04 | 645-07-05 | 645-07-06 |
|---|---|---|---|---|---|---|
| Foam Appearance (Initial) |  |  |  |  |  |  |
| Foam Appearance (After 1 minute) |  | 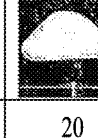 |  |  |  |  |
| % Neutralization | 10 | 20 | 30 | 40 | 50 | 60 |

FIG. 2A

Table 4 - Foam Stability - Rheological Characterisation (at 20 °C)

| Batch # | % Neutralization | Initial Viscosity [Pas] | Average Viscosity [Pas] | Final Viscosity [Pas] | Yield Stress [Pa] | Viscosity Change [Pas] | Foam Stability Value [FSV] |
|---|---|---|---|---|---|---|---|
| 645-07-01 | 10 | 0.262 | 0.077 | 0.000 | 1.609 | 0.262 | 0.0.36 |
| 645-07-02 | 20 | 0.404 | 0.107 | 0.000 | 2.774 | 0.404 | 0.130 |
| 645-07-03 | 30 | 4.944 | 0.704 | 3.139 | 52.046 | 1.805 | 12.348 |
| 645-07-04 | 40 | 7.656 | 0.000 | 0.000 | 89.956 | 7.656 | 0.000 |
| 645-07-05 | 50 | 7.339 | 0.407 | 0.844 | 66.053 | 6.495 | 165.405 |
| 645-07-06 | 60 | 7.803 | 1.023 | 1.982 | 71.479 | 5.821 | 362.881 |

FIG. 2B

Table 6 - Foam Stability - Appearance & Static Stability (at Room Temperature ~ 20 °C)

| Batch # | 651-04-02 | 651-04-03 | 651-04-04 | 651-04-05 | 651-04-06 | 651-04-07 |
|---|---|---|---|---|---|---|
| Foam Appearance (Initial) | | | | | | |
| Foam Appearance (After 1 minute) | | | | | | |
| % Neutralization | 22.7 | 25.9 | 29.1 | 32.2 | 35.4 | 38.5 |

FIG. 3A

Table 7 - Foam Stability - Rheological Characterisation (at 20 °C)

| Batch # | % Neutralization | Initial Viscosity [Pas] | Average Viscosity [Pas] | Final Viscosity [Pas] | Yield Stress [Pa] | Viscosity Change [Pas] | Foam Stability Value [FSV] |
|---|---|---|---|---|---|---|---|
| 651-04-02 | 22.7 | 0.714 | 0.253 | 0.476 | 2.843 | 0.238 | 0.188 |
| 651-04-03 | 25.9 | 3.811 | 0.059 | 0.207 | 42.445 | 3.604 | 8.339 |
| 651-04-04 | 29.1 | 2.821 | 0.483 | 1.278 | 23.071 | 1.543 | 17.943 |
| 651-04-05 | 32.2 | 2.954 | 0.462 | 1.224 | 29.802 | 1.730 | 24.819 |
| 651-04-06 | 35.4 | 5.157 | 0.759 | 3.565 | 46.208 | 1.592 | 55.427 |
| 645-04-07 | 38.5 | 8.746 | 0.370 | 3.497 | 91.865 | 5.249 | 169.082 |

FIG. 3B

FATTY ACID PHARMACEUTICAL FOAM

This is a Continuation Application of U.S. patent application Ser. No. 11/826,199, filed Jul. 12, 2007, an application claiming the benefit from U.S. Patent Application No. 60/830,949 filed Jul. 14, 2006, the contents of each of which are hereby incorporated by reference in their entirety.

There are many challenges in the topical application of pharmaceutically active agents. One major objective is to achieve percutaneous penetration of the active agent to the site of treatment. The composition should also be cosmetically elegant and should not cause irritation, discomfort, or inconvenience.

Lotion and gel topical dosage forms have the disadvantage of extended rub-in, they may leave oily residues and are less suitable for application to large surface areas. A solution dosage form readily runs off the site of application, and therefore it is difficult to apply controlled amounts of this type of dosage form.

The foamable compositions of the present invention break easily with shear and thus are suitable for the convenient topical delivery of a pharmaceutically active agent. These compositions may clearly be distinguished from traditional shaving cream foams which persist and require extended rub-in. Furthermore, the present compositions are cosmetically elegant, and are suitable for both application to large surface areas and targeted application to smaller areas.

BRIEF SUMMARY OF THE INVENTION

According to a first aspect, the present invention provides a foamable composition, comprising: water and an organic solvent, wherein the organic solvent comprises a $C_4$-$C_{30}$ fatty acid which is partially neutralized. According to an embodiment of the invention, the foamable composition further comprises a pharmaceutically active agent. The pharmaceutically active agent may be, for example, an immune response modifier compound, such as imiquimod. In a further embodiment, the pharmaceutically active agent is present in an amount of from about 0.0001% to about 40% by weight, based on the total weight of the foamable composition.

According to a preferred embodiment, the fatty acid is a $C_4$-$C_{24}$ fatty acid, more preferably a $C_8$-$C_{18}$ fatty acid, most preferably a $C_{18}$ fatty acid. $C_{18}$ fatty acids include, but are not limited to, stearic acid, isostearic acid, oleic acid, vaccenic acid, linoleic acid, alpha-linolenic acid, gamma-linolenic acid and eleostearic acid. According to a preferred embodiment, the $C_{18}$ fatty acid is isostearic acid or oleic acid. In one embodiment, the fatty acid is capric acid.

In certain other embodiments, the present invention provides a foamable composition wherein the organic solvent is present in an amount of from about 10% to about 50% by weight, based on the total weight of the foamable composition. According to a preferred embodiment, the organic solvent comprising a fatty acid is neutralized up to about 50% with a base, more preferably from about 0.01% to about 40%, still more preferably from about 10% to about 40%, and most preferably from about 20% to about 40%, such as 20%, 25%, 30%, 35% or 40%. The base can be, for example, an amine (e.g., triethanolamine), metal oxide, metal hydroxide, or the pharmaceutically active agent itself (in instances where the pharmaceutically active agent selected can act as a base), and mixtures thereof.

According to an embodiment of the invention, the compositions further comprise a surfactant. Suitable surfactants include, for example, a non ionic surfactant, a cationic surfactant, an anionic surfactant, a zwitterionic surfactant, an amphoteric surfactant or an ampholytic surfactant, and mixtures thereof.

According to an embodiment of the invention, the surfactant is present in an amount up to about 50% by weight, based on the total weight of the foamable composition. According to a further embodiment, the surfactant is present in an amount of up to 10% by weight, based on the total weight of the composition.

In an embodiment of the invention, water is present in an amount up to about 90% by weight, based on the total weight of the foamable composition (for example, from about 45% to about 90% by weight, based on the total weight of the foamable composition).

In still other embodiments, the compositions further comprise an emollient selected from the group consisting of an occlusive agent, an emollient oil, and a humectant. The emollient can be an occlusive agent such as a mineral oil, grease, petrolatum, an animal fat, a vegetable fat, a water insoluble polymer, a fatty alcohol, and mixtures thereof. In another embodiment, the occlusive agent is present in an amount of about 0.1% to about 55% by weight, or about 0.1% to about 10% by weight, based on the total weight of the foamable composition.

In other embodiments, the compositions further comprise a buffering agent or a pH adjusting agent.

In certain embodiments, the compositions further comprise at least one member selected from the group consisting of a viscosity reducer, a complexing agent, a gelling agent, an antioxidant, a thickener, a preservative, a corrosion inhibitor, a penetration enhancer, colors and fragrances.

In certain other embodiments, the compositions further comprise an aerosol propellant selected from the group consisting of a hydrocarbon, a chlorofluorocarbon, dimethyl ether, hydrofluorocarbons, and mixtures thereof. Preferably, the propellant comprises a mixture of hydrocarbons. In certain embodiments, the foamable composition is in a pressurized container. In one embodiment, the foamable composition is a foam when released from the pressurized container. In certain embodiments, the foam breaks easily with shear. In certain embodiments, the foam is homogenous. In one preferred embodiment, the present invention provides imiquimod as the pharmaceutically active agent in an amount of about 0.001% to 10% by weight; a $C_{18}$ fatty acid as the organic solvent in an amount of from about 10% to about 50% by weight; a base in an amount from about 0.01% to about 30% by weight; and water in an amount of about 45% to about 90% by weight.

According to a second aspect, the present invention provides a method for treating a dermatological disorder in a mammal, comprising: administering a foamable composition as herein described to treat the dermatological disorder.

These and other aspects, objects and advantages will become more apparent when read with the detailed description which follows.

BRIEF DESCRIPTION OF THE FIGURE

FIG. 2A illustrates the foam stability of various foams herein, in terms of appearance and static stability, at room temperature of about 20° C.

FIG. 2B illustrates the Rheological characterization of foam stability for the foams shown in FIG. 2A.

FIG. 3A illustrates the foam stability of various foams herein, in terms of appearance and static stability, at room temperature of about 20° C.

FIG. 3B illustrates the Rheological characterization of foam stability for the foams shown in FIG. 3A.

DETAILED DESCRIPTION OF THE INVENTION

I. Definitions

Figure 1:
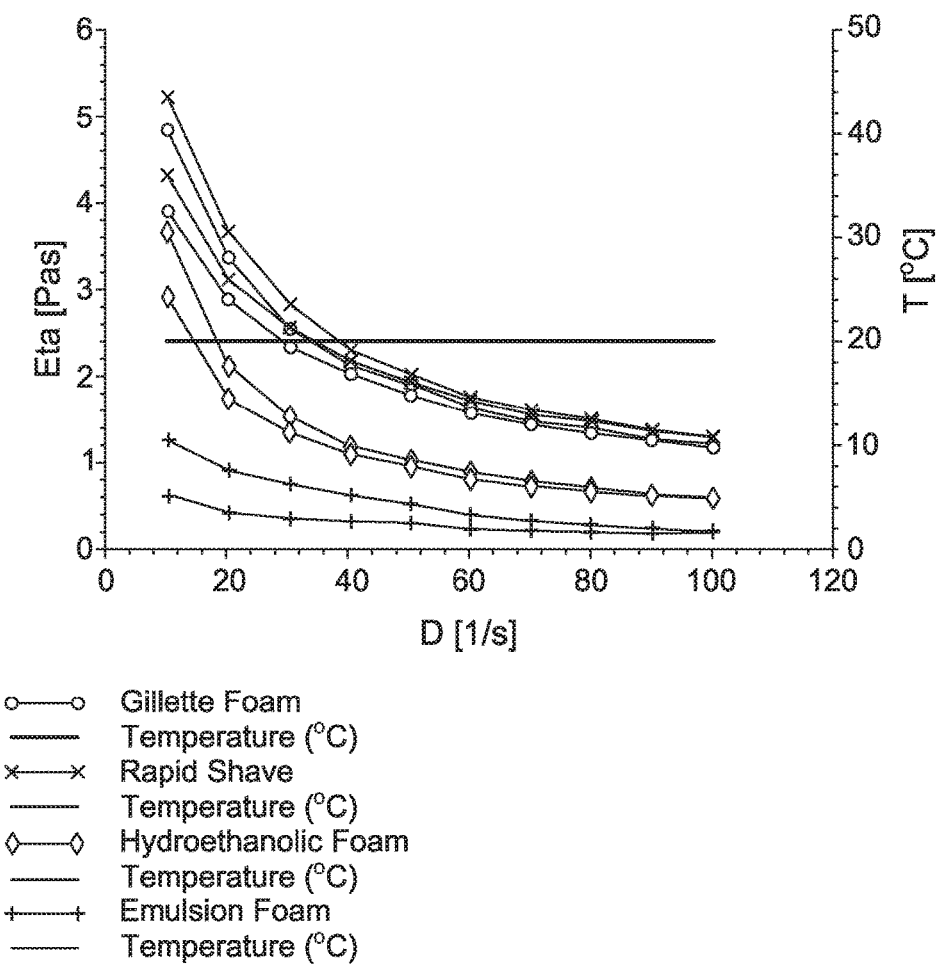
FIG. 1 illustrates the results of the rheological characterization of several different foam types (according to the prior art).

As used herein, the term "foamable" includes a composition that is capable of forming a foam.

As used herein, "pharmaceutically active agent" refers to a substance having a pharmaceutical, pharmacological or therapeutic effect. The pharmaceutically active agent may be in its free base or acid form, or in the form of salts, esters, solvates, or any other pharmaceutically acceptable derivatives, or as analogs, metabolites, pro-drugs, or components of molecular complexes.

As used herein, "immune response modifier compound" includes a compound which induces the production of one or more cytokines, e.g., Interferon ($\alpha$), Tumor Necrosis Factor, and Interleukin-12, from hematopoietic cells including dendritic cells and/or monocyte/macrophages. Examples of such compounds include the CpG oligonucleotides, lipopolysaccharides, polyinosic:polycytidylic acid complexes, and polypeptides and proteins known to induce cytokine production from dendritic cells and/or monocyte/macrophages. Immune response modifier compounds, immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imidazoquinoline amines such as imiquimod. One of skill in the art will appreciate that other immune response modifier compounds are useful in the present invention.

As used herein, the term "organic solvent" includes water-miscible or -immiscible solvents capable of dissolving either or both of water-soluble and water-insoluble organic compounds. Examples of water-miscible solvents useful in the present invention include, but are not limited to, short chained alcohols (e.g. ethanol and isopropanol), polyols (e.g. glycerol) and glycols (e.g. propylene glycol, polyethylene glycol, hexylene glycol, 1,3-butylene glycol and dipropylene glycol). Examples of water-immiscible solvents useful in the present invention include, but are not limited to, an ester such as isopropyl myristate, C12-C15 alkyl benzoate, caprylic/capric glyceride or caprylic/capric triglyceride; a medium to long chain alcohol such as dodecanol or myristyl alcohol; an aromatic and/or alkyl pyrrolidone such as lauryl pyrrolidone; an aromatic and/or alkyl and/or cyclic ketone; an aromatic and/or alkyl and/or cyclic ether; substituted and/or unsubstituted aromatic; straight chain and/or branched chain and/or cyclic alkane or silicone. One of skill in the art will appreciate that other organic solvents are useful in the present invention.

As used herein, the term "fatty acid" includes a carboxylic acid having an aliphatic tail, typically from 4 to 30 carbon atoms long. Fatty acids can be saturated, mono-unsaturated or poly-unsaturated. Fatty acids can be straight chain or branched. Examples of fatty acids useful in the present invention, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linolenic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). One of skill in the art will appreciate that other fatty acids are useful in the present invention.

As used herein, the term "fatty acid derivative" includes a fatty acid compound that has been modified by one or several chemical reactions, or a salt thereof. For example, the carboxylic acid can be esterified, or converted to an amide. In addition, the carboxylic acid can be protected with a protecting group known to one of skill in the art, or reduced to an aldehyde or alcohol. One of skill in the art will appreciate that other fatty acid derivatives are useful in the present invention.

As used herein, the term "amine" includes ammonia, tri-alkyl amines such as triethyl amine, and ethanolamine. Other examples include tromethamine, dimethyl stearamine and PEG 15 cocamine. One of skill in the art will appreciate that other amines are useful in the present invention.

As used herein, the term "metal oxide" includes the oxide of any alkaline earth metal such as Be, Mg, Ca, Sr and Ba. Other useful metals include transition metals such as Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac, as well as post-transition metals such as Al, Ga, In, Tl, Ge, Sn, Pb, Sb, Bi, and Po. Exemplary metal oxides include, but are not limited to, MgO and $Al_2O_3$. One of skill in the art will appreciate that other metal oxides are useful in the present invention.

As used herein, the term "metal hydroxide" includes a compound of the formula $(M^{n+})_x(OH)_{xn}$, wherein the metal (M) can be any alkaline earth metal such as Be, Mg, Ca, Sr and Ba. Other useful metals include transition metals such as Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac, as well as post-transition metals such as Al, Ga, In, Tl, Ge, Sn, Pb, Sb, Bi, and Po. Exemplary metal hydroxides include, but are not limited to, NaOH, KOH, $Al(OH)_3$ and CsOH. One of skill in the art will appreciate that other metal hydroxides are useful in the present invention.

As used herein, the term "surfactant" includes any agent that alters the surface properties of the oil and water components in the composition to aid in the formation of an emulsion. Surfactants useful in the present invention include, but are not limited to, a non-ionic surfactant, a cationic surfactant, an anionic surfactant, a zwitterionic surfactant, an amphoteric surfactant, or an ampholytic surfactant, and mixtures thereof. A surfactant's hydrophilic/lipophilic balance (HLB) describes the surfactant's affinity toward water or oil (1-20, with 1 being lipophilic and 20 being hydrophilic). The HLB of a blend of two surfactants equals the weight fraction of surfactant A times its HLB value plus the weight fraction of surfactant B times its HLB value (weighted average). According to one or more embodiments of the present invention, the surface-active agent has a hydrophilic lipophilic balance (HLB) between about 9 and about 14, which is the required HLB (the HLB required to stabilize an o/w emulsion of a given oil) for most oils and hydrophobic solvents. Examples of non-ionic surfactants useful in the present invention include, but are not limited to, include fatty alcohols, fatty alcohol derivatives and fatty acid derivatives. Anionic surfactants useful in the present invention include, but are not limited to, soaps including alkali soaps, such as sodium, potassium and ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride and quaternary ammonium compounds such as benzalkonium chloride. One of skill in the art will appreciate that other surfactants are useful in the present invention.

As used herein, the term "fatty alcohol" includes an alcohol having an aliphatic tail, typically from 4 to 30 carbon atoms long. Fatty alcohols can be saturated, mono-unsaturated, poly-unsaturated, linear or branched. Examples of fatty alcohols useful in the present invention include, but are not limited to, lauryl alcohol (C12), tetradecanol (C14), pentadecanol (C15), cetyl alcohol (C16), stearyl alcohol (C18), oleyl alcohol (C18), eicosanol (C20) and behenyl alcohol (C22). Fatty alcohols of the present invention are useful as an emollient, a bodying agent, a foam stabilizer and a surfactant, among others. One of skill in the art will appreciate that other fatty alcohols are useful in the present invention.

As used herein, the term "fatty alcohol derivative" includes a fatty alcohol compound that has been modified by one or several chemical reactions. For example, the alcohol can be oxidized to a carbonyl compound such as an aldehyde or carboxylic acid. In addition, the alcohol could be protected with a suitable protecting group known to one of skill in the art. Other derivatives can include esters or ethers formed using a fatty alcohol. One of skill in the art will appreciate that other fatty alcohol derivatives are useful in the present invention.

As used herein, the term "sorbitan ester" includes an ester of sorbitol and a fatty acid. Sorbitan esters useful in the present invention include, but are not limited to, sorbitan monolaurate (Arlacel 20), sorbitan monopalmitate (Span-40), sorbitan monooleate (Span-80), sorbitan monostearate and sorbitan tristearate. One of skill in the art will appreciate that other sorbitan esters are useful in the present invention.

As used herein, the term "polyoxyethylene fatty alcohol ether" includes an ether formed from a polyoxyethylene polymer chain and a fatty alcohol. Any of the fatty alcohols described above are useful as polyoxyethylene fatty alcohol ethers of the present invention. In addition, the polyoxyethylene segments can have from 5 to about 100 ethylene oxide units. Polyoxyethylene fatty alcohol ethers useful in the present invention include, but are not limited to, polyoxyethylene (20) stearyl ether and polyoxyethylene (20) cetostearyl ether. One of skill in the art will appreciate that other polyoxyethylene fatty alcohol ethers are useful in the present invention.

As used herein, the term "emollient" includes an agent that softens, soothes and improves the lipid content of the skin or other mucous membranes. Emollients accomplish this by either slowing water loss from the skin through the use of an occlusive agent, improving the lipid content of the skin with an emollient oil, or by increasing the amount of water in the skin by use of a humectant. The occlusive agent in the foamable compositions of the present invention include, but are not limited to, a mineral oil, grease, petrolatum, an animal fat, a vegetable fat, a water insoluble polymer, a fatty alcohol, and mixtures thereof. Examples of emollient oils include isostearic acid derivatives, isopropyl palmitate, lanolin oil, diisopropyl dimerate, diisopropyl adipate, dimethyl isosorbide, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristyl myristate, triisocetyl citrate, octyl dodecanol, octyl hydroxystearate, and mixtures thereof. Humectants are characterized as having several hydrophilic functional groups. Humectants useful in the foamable compositions of the present invention include, but are not limited to, propylene glycol and polyols such as sorbitol, maltitol and polymeric polyols such as polydextrose. Other examples of suitable emollients can be found in the Cosmetic Bench Reference, pp. 1.19-1.22 (1996). One of skill in the art will appreciate that other emollients are useful in the present invention.

As used herein, the term "buffering agent" includes any inorganic or organic acid or base that resists changes in pH and maintains the pH around a desired point. Buffering agents useful in the present invention include, but are not limited to, sodium hydroxide, dibasic sodium phosphate anhydrous, and mixtures thereof. One of skill in the art will appreciate that other buffering agents are useful in the present invention.

As used herein, the term "viscosity reducer" includes an agent that reduces the viscosity of the composition. Viscosity reducers useful in the foamable compositions of the present invention include, but are not limited to, isopropyl myristate, light mineral oil and cyclomethicone, and mixtures thereof. One of skill in the art will appreciate that other viscosity reducers are useful in the present invention.

As used herein, the term "complexing agent" includes an agent that is capable of complexing to other components of the composition. Complexing agents useful in the foamable compositions of the present invention include, but are not limited to, edetate disodium dehydrate. One of skill in the art will appreciate that other complexing agents are useful in the present invention.

As used herein, the term "gelling agent" includes an agent that is capable of increasing the viscosity of the composition. Gelling agents can include, but are not limited to, natural gums, starches, pectins, sodium, potassium, ammonium, calcium, agar, carrageenan, locust bean gum and gelatin. One of skill in the art will appreciate that other gelling agents are useful in the present invention.

As used herein, the term "antioxidant" includes an agent that prevents the oxidation of other compounds. Examples of antioxidants useful in the compositions of the present invention include, but are not limited to, beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, 1-carnitine, phenoxyethanol, butylated hydroxytoluene and sodium benzoate. One of skill in the art will appreciate that other antioxidants are useful in the present invention.

As used herein, the term "thickener" includes substances which, when added to a mixture, increase its viscosity without substantially modifying its other properties. Thickeners provide body, increase stability, and improve suspending action. Thickeners useful in the compositions of the instant invention include, but are not limited to, agar, alginin, arrowroot, collagen, cornstarch, fecula, gelatin, guar gum, katakuri, locust bean gum, pectin, roux, tapioca, and xanthan gum. One of skill in the art will appreciate that other thickeners are useful in the present invention.

As used herein, the term "aerosol propellant" includes a gas that assists in propelling the foamable composition out of a pressurized container. The aerosol propellant can be any suitable gas or mixture thereof, such as a hydrocarbon, a chlorofluorocarbon, dimethyl ether, hydrofluorocarbons, and mixtures thereof. Hydrocarbon propellants include, but are not limited to, propane, n-butane and isobutane. Chlorofluorocarbons are alkanes where the hydrogens have been replaced with chlorine and fluorine atoms. Exemplary chlorofluorocarbons include, but are not limited to, chlorofluoromethanes such as trichlorofluoromethane and dichlorodifluoromethane, and chlorofluoroethanes such as trichlorotrifluoroethane. Hydrofluorocarbons are alkanes where some hydrogens have been replaced with fluorine atoms, but some hydrogen atoms remain. Exemplary hydrofluorocarbons include, but are not limited to, hydrofluoromethanes such as trifluoromethane, and hydrofluoroethanes such as tetrafluoroethane. One of skill in the art will appreciate that other aerosol propellants are useful in the present invention.

As used herein, the term "treat" or "treating" includes any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "dermatological disorder" includes an abnormal skin condition such as those described below.

The term "foamable" refers to the composition being able to form a foam. It can be worked into a foam, for example, following application to wet or dry skin. It can form a foam when dispensed from a device that allows air or vapor to be entrapped within the composition during dispensing, for example, an air aspirated foaming dispenser. It can form a foam when dispensed from an aerosol container, for example, wherein a liquefied propellant mixed with the composition facilitates the production of a foam.

II. Foamable Compositions

The present invention provides a foamable composition comprising water and an organic solvent, wherein the organic solvent comprises a $C_4$-$C_{30}$ fatty acid which is partially neutralized.

A pharmaceutically active agent may be incorporated in one or more phases of the foamable composition. The most appropriate phase of incorporation will depend on the solubility characteristics of the pharmaceutically active agent and the desired release characteristics of the pharmaceutically active agent from the foamable composition.

A. Pharmaceutically Active Agent

Examples of suitable pharmaceutically active agents include, but are not limited to, immune response modifier compounds, retinoids, vitamin D analogs, corticosteroids, antihistamines, antimicrobial agents, antifungal agents, antimalarial agents, antivirals, cytotoxic agents, psoralens, minoxidil, anti-androgens, antipruritic agents, keratolytic agents, tars, dithranol, antiseptics, sunscreens, anaesthetics and analgesics, and skin conditioning and nutritional agents, and mixtures thereof.

Immune response modifier compounds, immunosuppressant agents, immunoregulating agents and immunomodulators are chemically or biologically-derived agents that modify the immune response or the functioning of the immune system (as by the stimulation of antibody formation or the inhibition of white blood cell activity). Immune response modifier compounds, immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imidazoquinoline amines such as imiquimod, and mixtures thereof.

Additional compounds include imidazoquinoline amines, imidazopyridine amines, 6,7-fused cycloalkylimidazopyridine amines, imidazonaphthpyridine amines, tetrahydroimidazonaphthpyridine amines, oxazolopyridine amines, oxazoloquinoline amines, thiazolopyridine amines, thiazoloquinoline amines and 1,2-bridged imidazoquinoline amines. Such compounds and methods for preparing them are disclosed in, for example, U.S. Pat. Nos. 4,689,338; 5,389,640; 5,268,376; 4,929,624; 5,266,575; 5,352,784; 5,494,916; 5,482,936; 5,395,937; 5,175,296; 5,693,811; 5,741,908; 5,756,747; 6,110,929; 4,988,815; 5,376,076; 6,083,505; 6,039,969; and International Publications WO 99/29693; WO 00/76505; WO 00/76518 and WO 00/76518. Preferred compounds include 1-(2-methylpropyl)-1H-imidazo[4,5-c]quinolin-4-amine (imiquimod), 4-amino-2-ethoxymethyl-α,α-dimethyl-1H-imidazo[4,5-c]quinoline-1-ethanol (resiquimod), and 2-propyl[1,3]thiazolo[4,5-c]quinolin-4-amine.

Additional compounds useful in the present invention, include those of the following formula:

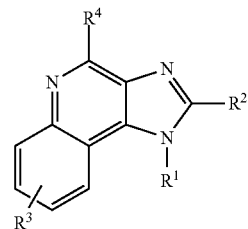

wherein $R^1$, $R^2$ and $R^3$ are each independently selected from the group consisting of hydrogen, alkyl containing one to six carbon atoms and hydroxyalkyl containing one to six carbon atoms. $R^4$ is an amine optionally substituted with an alkyl containing one to six carbon atoms and hydroxyalkyl containing one to six carbon atoms. Alternatively, the compound is in a pharmaceutically acceptable salt form.

In one embodiment of the present invention, the immune response modifier compound is an imidazoquinoline amine. In another embodiment, the immune response modifier compound is imiquimod.

In some embodiments of the present invention, the immune response modifier compound is present in amounts from approximately 0.0001% by weight to approximately 10% by weight, based on the total weight of the foamable composition. In other foamable compositions, the immune response modifier compound is present in amounts from approximately 0.001% to approximately 1% by weight. In still other foamable compositions, the immune response modifier compound is present in amounts from approximately 0.001% to approximately 0.1% by weight. In another foamable composition, the immune response modifier compound is present in amounts from approximately 0.001% to approximately 0.01% by weight. One of skill in the art will appreciate that foamable compositions having other amounts of the immune response modifier compound are useful in the present invention.

Exemplary retinoids include, but are not limited to, tretinoin, isotretinoin, etretinate, acitretin, adapalene and tarazotene, and mixtures thereof. Exemplary vitamin D analogs include, but are not limited to, calcidiol, calcitriol, calcipotriene, paricalcitol, 22-oxacolcitriol, dihydrotachysterol, calciferol, and those listed in U.S. Pat. No. 6,787,529, and mixtures thereof.

Exemplary corticosteroids useful in the present invention include, but are not limited to, alclometasone dipropionate, amcinonide, beclamethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone preparations, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, and mixtures thereof.

Exemplary antihistamines include, but are not limited to, cetirizine, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, and chlorpheniramine, and mixtures thereof.

Exemplary antimicrobial agents include, but are not limited to, amikacin, bacitracin, colistin, gentamicin, kanamycin, metronidazole, clindamycin, erythromycin, tetracycline, doxycycline, minocycline, dapsone, sulfapyridine, mupirocin, neomycin, netilmicin, polymyxin B, streptomycin, tobramycin, phenols and cresols such as 2,4-dichloro-symmetaxylenol, parachlorometaxylenol, and parachlorometacresol, bisphenols such as hexachlorophene, dichlorophene, bithionol, triclosan, and fentichlor, salicylanilides such as 4',5-dibromsalicylanilide, 3',4',5-trichlorosalicylanilide, 3',4',5-tribromosalicylanilide, and 3,5,dibromo-3'-trifluoromethyl-salicylanilide, carbanilides such as trichlorocarbanilde and 3-trifluoromethyl-4-4'-dichlorocarbanilide, quaternary ammonium compounds such as alkyl-dimethyl benzyl ammonium chloride, alkyl-trimethyl ammonium chloride, alkyl trimethyl ammonium bromide, cetyl-trimethyl ammonium bromide, B-phenoxyethyl-dimethyl-dodecyl ammonium bromide, p-tert-octylphenoxyethoxyethyl-dimethylbenzyl ammonium chloride, tetradecyl-pyridinium bromide, cetyl pyridinium bromide, cetyl pyridinium chloride, di-(n-octyl)-dimethyl ammonium bromide, alkyl-isoquinolinium bromide, 1-(3-chloroallyl)-3-5 7-triaza-1-azoniaadamantane chloride, and chlorhexidine (1,6,di(N-p-chlorophenylguanidino)hexane), 2-bromo-2-nitropropan-1,3-diol, imidazonidyl urea, ethanol, isopropyl alcohol, and mixtures thereof.

Exemplary antifungal agents include, but are not limited to, those selected from the group consisting of imidazoles, hydroxy pyridones, triazoles, allyl amines, undecylenic acid derivatives, tolnaftate, haloprogin, pyridinethiones, cloquinol, amphotericin B, butoconazole nitrate, ciclopiroxolamine, clindamycin, clioquinol, clotrimazole, econazole, econazole nitrate, fluconazole, flucytosine, griseofulvin, itraconazole, ketoconazole, albaconazole, miconazole, micronazole, naftifine, nystatin, omadine disulfide, sulconazole, terbinafine, terconazole, tioconazole, tolnaftate, triacetin, unecylenic acid, zinc pyrithione, and mixtures thereof.

Exemplary antimalarial agents include, but are not limited to, 4-aminoquinolines, ∝-aminoquinolines, chloroquine, hydroxychloroquine and pyrimethamine, and mixtures thereof.

Exemplary antivirals include, but are not limited to, aciclovir, carbovir, desciclovir, famciclovir, foscarnet sodium, ganciclovir sodium, interferons, penciclovir, valaciclovir hydrochloride, and mixtures thereof.

Exemplary cytotoxic agents include, but are not limited to, azathioprine, cyclophosphamide, cyclosporine, methotrexate, hydroxyurea, thalidomide, bleomycin and fluorouracil, and mixtures thereof.

An exemplary psoralen is methoxsalen.

Exemplary anti-androgens include, but are not limited to, spironolactone, cyproterone acetate, flutamide and finasteride, and mixtures thereof.

Exemplary antipruritics include, but are not limited to, calamine, camphor and menthol, and mixtures thereof.

Exemplary keratolytic agents include, but are not limited to, salicylic acid, benzoic acid, urea and propylene glycol, and mixtures thereof.

Exemplary tars include, but are not limited to, coal tar, pine tar and ichthammol, and mixtures thereof.

Exemplary antiseptics include, but are not limited to, benzoyl peroxide, hydrogen peroxide, chlorhexidine, cetrimide, povidone iodine and triclosan, and mixtures thereof.

Exemplary sunscreens include, but are not limited to, p-aminobenzoic acid and its derivatives (ethyl, isobutyl, glycerly esters), p-dimethylaminobenzoic acid and its derivitatives (ethyl, isobutyl, glyceryl esters), o-aminobenzoates and its derivatives (methyl, menthyl, phenyl, benzyl, phenylethyl, linaly, terpenyl, and cyclohexenyl esters), salicylates (amyl, phenyl, benzyl, menthyl, glyceryl, and dipropylene-glycol esters), cinnamic acid derivatives (menthyl and benzyl esters; alphphenyl cinnamonitrile; butly cinnamoyl pyruvate, 2-ethylhexyl p-methoxycinnamate, iso-amyl p-methoxycinnamate), dihydroxycinnamic acid derivatives (umbelliferone, methyl-umbelliferone, methylaceto-umbelliferone), trihydroxycinnamic acid derivatives (esculetin, methylesculetin, daphnetin), hydrocarbons (diphenylbutadiene, stilbene), dibenzalacetone, benzalacetophenone, naphthosulphonates (sodium salts of 2-naphthol-3,6-disulphonic acid and of 2-naphthol-6,8-disulphonic acid), organic benzophenone derivatives (2,4-dihydroxybenzophenone, 2,2',4,4'-tetrahydroxybenzophenone, 2-hydroxy-4-methoxybenzophenone, 2-hydroxy-4-methoxybenzophenone-5-sulfonic acid, 2,2'-dihydroxy-4,4'-dimethoxybenzophenone, 2,2'-dihydroxy-4-methoxybenzophenone, disodium 2,2'-dihydroxy-4,4'-dimethoxy-5,5'-disulfobenzophenone), zinc oxide, titanium dioxide, and mixtures thereof.

Exemplary anaesthetics and analgesics include, but are not limited to, benzocaine lidocaine, lignocaine, prilocaine and choline salicylate, and mixtures thereof.

Exemplary skin-conditioning agents include, but are not limited to, hydrocarbon oils and waxes, silicones, fatty acid derivatives, cholesterol, cholesterol derivatives, di- and tri-glycerides, vegetable oils, vegetable oil derivatives, liquid nondigestible oils such as those described in Mattson, U.S. Pat. No. 3,600,186 and Jandacek et al., U.S. Pat. Nos. 4,005,195 and 4,005,196, all of which are herein incorporated by reference in their entirety, or blends of liquid digestible or nondigestible oils with solid polyol polyesters such as those described in Jandacek, U.S. Pat. No. 4,797, 300, and Letton, U.S. Pat. Nos. 5,306,514, 5,306,516, and 5,306,515, all of which are herein incorporated by reference in their entirety, acetoglyceride esters, alkyl esters, alkenyl esters, lanolin and its derivatives, milk tri-glycerides, wax esters, beeswax derivatives, sterols, phospholipids, and mixtures thereof. Exemplary nutritional agents include vitamins, essential amino acids, essential fats and antioxidants, and mixtures thereof.

Other pharmaceutically active agents commonly known as useful in the preparation of topical pharmaceutical compositions are further contemplated as within the scope of the present invention and the entire content of "Martindale, The Extra Pharmacopoeia", 31$^{st}$ Edition is incorporated herein by reference.

B. Organic Solvent

The foamable compositions of the present invention comprise organic solvent, wherein the organic solvent comprises a $C_4$-$C_{30}$ fatty acid which is partially neutralized. The term "fatty acid" refers to a carboxylic acid having an aliphatic tail, typically from 4 to 30 carbon atoms long. Fatty acids can be saturated, mono-unsaturated or poly-unsaturated. Fatty acids can be straight chain or branched. Branched fatty acids include iso-fatty acids that have a branch point at the penultimate carbon (one carbon from the chain end) as well as anteiso-fatty acids (one carbon from the penultimate carbon).

Fatty acids useful in the compositions of the present invention include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linolenic acid (C18), gamma-linolenic acid (C18), eleostearic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). Preferred fatty acids are $C_4$-$C_{24}$ fatty acids. More preferred fatty acids are $C_8$-$C_{18}$ fatty acids. Most preferred fatty acids are $C_{18}$ fatty acids. Preferred $C_{18}$ fatty acids useful in the present invention are stearic acid, isostearic acid, oleic acid, vaccenic acid, linoleic acid, alpha-linolenic acid, gamma-linolenic acid and eleostearic acid. In still other embodiments, the fatty acid is an iso-fatty acid such as iso-stearic acid. In other embodiments, the fatty acid is capric acid. The organic solvents of the present invention are present in an amount of from about 10% to about 50% w/w, based on the total weight of the foamable composition. One of skill in the art will appreciate that other fatty acids and their derivatives are useful in the present invention.

The foamable compositions of the present invention may comprise organic solvent in addition to the $C_4$-$C_{30}$ fatty acid. This additional organic solvent may be water-miscible or water-immiscible. A water-miscible solvent may, for example, act as a humectant, a penetration enhancer, or as a cosolvent to effect dissolution of the pharmaceutically active agent into the water phase. The water-immiscible solvent may, for example, act as an emollient, a penetration enhancer, or as a cosolvent to effect dissolution of the pharmaceutically active agent into the fatty acid based oil phase. Examples of water-miscible solvents useful in the present invention include, but are not limited to, short chained alcohols (e.g. ethanol and isopropanol), polyols (e.g. glycerol) and glycols (e.g. propylene glycol, polyethylene glycol, hexylene glycol, 1,3-buytlene glycol and dipropylene glycol). Examples of water-immiscible solvents useful in the present invention include, but are not limited to, esters such as isopropyl myristate, $C_{12}$-$C_{15}$ alkyl benzoate, caprylic/capric glyceride or caprylic/capric triglyceride; a medium to long chain alcohol for example dodecanol or myristyl alcohol; an aromatic and/or alkyl pyrrolidone such as lauryl pyrrolidone; an aromatic and/or alkyl and/or cyclic ketone; an aromatic and/or alkyl and/or cyclic ether; substituted and/or unsubstituted aromatic; straight chain and/or branched chain and/or cyclic alkane or silicone.

The fatty acid organic solvents of the present invention are partially neutralized by the addition of a base. In some embodiments, the fatty acid organic solvent is neutralized up to 50% with a base. In preferred embodiments, the fatty acid organic solvent is neutralized from about 20% to about 40% with a base. It is thought that the partially neutralized fatty acid acts as an in situ surfactant, thus emulsifying the un-neutralized fatty acid within the water phase. This, in turn, permits the pharmaceutically active agent to be incorporated into one or more phases of the composition, including the water phase, the dispersed fatty acid based oil phase and the surfactant micelles.

The base used to neutralize the fatty acid organic solvent can be an amine, a metal oxide, a metal hydroxide or the pharmaceutically active agent (in instances where the pharmaceutically active agent selected can act as a base), and mixtures thereof. Amines useful as a base in the present invention include, but are not limited to, ammonia, tri-alkyl amines such as triethyl amine, and ethanolamine. The metal part of the metal oxide and metal hydroxide bases can be any alkaline earth metal such as Be, Mg, Ca, Sr and Ba. Other useful metals include transition metals such as Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac, as well as post-transition metals such as Al, Ga, In, Tl, Ge, Sn, Pb, Sb, Bi, and Po. Exemplary metal oxides include, but are not limited to, MgO and $Al_2O_3$. Exemplary metal hydroxides include, but are not limited to, CsOH, KOH, NaOH and $Al(OH)_3$.

The solvent of the present invention may comprise a mixture of two or more of the above organic solvents in any proportion. One of skill in the art will appreciate that other organic solvents are useful in the present invention.

C. Surfactants

The foamable compositions of the present invention can also comprise a surfactant, in addition to the surfactant generated in situ by the partial neutralization of the fatty acid. Surfactants useful in the present invention include, but are not limited to, a non-ionic surfactant, a cationic surfactant, an anionic surfactant, a zwitterionic surfactant, an amphoteric surfactant, or an ampholytic surfactant, and mixtures thereof.

Surfactants include any agent that alters the surface properties of the oil and water components in the composition to aid in the formation of an emulsion. A surfactant's hydrophilic/lipophilic balance (HLB) describes the surfactant's affinity toward water or oil. The HLB scale ranges from 1 (totally lipophilic) to 20 (totally hydrophilic), with 10 representing an equal balance of both characteristics. Lipophilic surfactants tend to form water-in-oil (w/o) emulsions; hydrophilic surfactants tend to form oil-in-water (o/w) emulsions. The HLB of a blend of two surfactants equals the weight fraction of surfactant A times its HLB value plus the weight fraction of surfactant B times its HLB value (weighted average).

Any surfactant, selected from non-ionic, cationic, anionic, zwitterionic, amphoteric and ampholytic surfactants, or combinations thereof may be used. According to one or more embodiments of the present invention, the surface-active agent has a hydrophilic lipophilic balance (HLB) between about 9 and about 14, which is the required HLB (the HLB required to stabilize an o/w emulsion of a given oil) of most oils and hydrophobic solvents. Thus, in one or more embodiments, the composition has a single surface active agent having an HLB value between about 9 and 14, and in one or more embodiments, the foam composition contains more than one surface active agent and the weighted average of their HLB values is between about 9 and about 14.

Non-ionic surfactants useful in the present invention include, but are not limited to, fatty alcohols, fatty alcohol derivatives and fatty acid derivatives. Fatty alcohols useful as surfactants in the present invention include, but are not limited to, lauryl alcohol (C12), tetradecanol (C14), pentadecanol (C15), cetyl alcohol (C16), stearyl alcohol (C18), oleyl alcohol (C18), eicosanol (C20) and behenyl alcohol (C22). Fatty alcohol derivatives useful as non-ionic surfactants also include, but are not limited to, ethers of polyethylene glycol and fatty alcohols such as PEG-3 oleyl ether (Volpo 3) and PEG-4 lauryl ether (Brij 30). Other PEG-ethers include ceteareth-20, formed from cetearyl alcohol and PEG-20. Cetearyl alcohol is a mixture of cetyl alcohol and stearyl alcohol.

Fatty acid derivatives useful as non-ionic surfactants include, but are not limited to, glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether and polyoxyethylene (20) cetostearyl ether, polyoxyethylene sorbitan fatty acid esters such as polyoxyethylene sorbitan monostearate, sorbitan esters such as sorbitan monolaurate (Arlacel 20), sorbitan monopalmitate (Span-40), sorbitan monooleate (Span-80), sorbitan monostearate and sorbitan tristearate, alkyl glycosides such as cetearyl glucoside, fatty acid ethanolamides and their derivatives such as the diethanolamide of stearic acid, ethoxylated fatty acids, ethoxylated hydrogenated fatty acids, and the like.

Exemplary non-ionic surfactants include polyethoxylated fatty acids, fatty acid diesters, polyethylene glycol glycerol fatty acid esters, alcohol-oil transesterification products, polyglycerized fatty acids, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters and lower alcohol fatty acid esters.

Additional surfactants useful in the present invention include polysorbates, such as polyoxyethylene (20) sorbitan monostearate (Tween 60) and poly (oxyethylene) (20) sorbitan monooleate (Tween 80); poly (oxyethylene) (POE) fatty acid esters, such as Myrj 45, Myrj 49 and Myrj 59; poly (oxyethylene) alkylyl ethers, such as poly (oxyethylene) cetyl ether, poly (oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides and isoceteth-20.

Additional surfactants include PEG-fatty acid esters. Exemplary monoesters include esters of lauric acid, oleic acid, and stearic acid, e.g., PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Polyethylene glycol fatty acid diesters suitable for use as non-ionic surfactants in the compositions of the present invention include PEG-20 dilaurate, PEG-20 dioleate, PEG-20 distearate, PEG-32 dilaurate and PEG-32 dioleate. Suitable polyethylene glycol glycerol fatty acid esters include PEG-20 glyceryl laurate, PEG-30 glyceryl laurate, PEG-40 glyceryl laurate, PEG-20 glyceryloleate, and PEG-30 glyceryl oleate.

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® b M 2735 CS), PEG-8 corn oil (Labrafil® WL 2609 BS), PEG-20 corn glycerides (Crovol M40), and PEG-20 almond glycerides (Crovol A40). The latter two surfactants are reported to have HLB values of 10, which is generally considered to be the approximate border line between hydrophilic and hydrophobic surfactants.

Alcohol-oil transesterification derivatives of oil soluble vitamins (e.g., vitamins A, D, E, K, etc.), such as tocopheryl PEG-100 succinate (TPGS, available from Eastman), are also suitable surfactants.

Polyglycerol esters of fatty acids are also suitable non-ionic surfactants for the present invention. Among the polyglyceryl fatty acid esters, exemplary use hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Polyglyceryl polyricinoleates (Polymuls) are hydrophilic and hydrophobic surfactants of this class.

Sterols and derivatives of sterols are suitable surfactants for use in the present invention. These surfactants can be hydrophilic or hydrophobic. Preferred derivatives include the polyethylene glycol derivatives. An exemplary hydrophobic surfactant in this class is cholesterol. An exemplary hydrophilic surfactant in this class is PEG-24 cholesterol ether (Solulan C-24).

A variety of PEG-sorbitan fatty acid esters are suitable for use as non-ionic surfactants in the present invention. In general, these surfactants are hydrophilic, although several hydrophobic surfactants of this class can be used. Among the PEG-sorbitan fatty acid esters, exemplary hydrophilic surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80).

The polyoxyethylene-polyoxypropylene (POE-POP) block copolymers are a unique class of polymeric surfactants. The unique structure of the surfactants, with hydrophilic POE and hydrophobic POP moieties in well-defined ratios and positions, provides a wide variety of surfactants suitable for use in the present invention. These surfactants are available under various trade names, including Synperonic PE series (ICI), Pluronic® series (BASF), Emkalyx, Lutrol (BASF), Supronic, Monolan, Pluracare, and Plurodac. The generic term for these polymers is "poloxamer" (CAS 9003-11-6). Exemplary hydrophilic surfactants of this class include Poloxamers 108,188, 217,238, 288,338, and 407. Exemplary hydrophobic surfactants in this class include Poloxamers 124, 182, 183, 212, 331, and 335.

In one or more embodiments of the present invention, the surface-active agent comprise mono-, di- and tri-esters of sucrose with food fatty acids (sucrose esters), prepared from sucrose and methyl and ethyl esters of food fatty acids or by extraction from sucroglycerides. Exemplary sucrose esters include sucrose monopalmitate and sucrose monolaurate. Suitable sucrose esters include those having a high monoester content, which have higher HLB values.

Anionic surfactants useful in the present invention include, but are not limited to, soaps including alkali soaps, such as sodium, potassium and ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Another class of useful soaps is the metallic soaps, salts of polyvalent metals and aliphatic carboxylic acids, usually fatty acids, such as aluminum stearate. Other classes of useful anionic surfactants include sulfated fatty acid alcohols such as sodium lauryl sulfate, sulfated oils such as the sulfuric ester of ricinoleic acid disodium salt, and sulfonated compounds such as alkyl sulfonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sulfonate such as aryl naphthalene with alkyl substitutes. One of skill in the art will appreciate that other anionic surfactants are useful in the present invention.

Cationic surfactants useful in the present invention include, but are not limited to, amine salts such as octadecyl ammonium chloride and quaternary ammonium compounds such as benzalkonium chloride. One of skill in the art will appreciate that other cationic surfactants are useful in the present invention.

Additional surfactants useful in the present invention include sodium methylcocoyl taurate, sodium methyl oleoyl taurate, sodium lauryl sulfate, triethanolamine lauryl sulfate and betaines.

Fatty acid salts are also useful, and include, but are not limited to, organic salts such as ammonium and alkyl-ammonium salts, as well as inorganic salts such as sodium, potassium, magnesium and calcium salts. One of skill in the art will appreciate that other fatty acids are useful in a variety of manners in the present invention.

The surfactant of the foamable composition of the present invention can be a single surfactant or a mixture of several different surfactants.

The surfactant of the foamable composition of the present invention can be present in any suitable stabilizing amount. In one embodiment, the surfactant is present in an amount up to about 50% by weight, based on the total weight of the composition. In other embodiments, the surfactant is present in an amount of approximately 0.1% to about 10% by weight. One of skill in the art will appreciate that other amounts of surfactant are useful in the present invention.

D. Water

Foamable compositions of the present invention comprise water in an amount up to 90% w/w, based on the total weight of the foamable composition. Some foamable compositions comprise water in an amount from about 45% to about 90% w/w, based on the total weight of the foamable composition. One of skill in the art will appreciate that foamable compositions having other amounts of water are useful in the present invention.

E. Emollient

Emollients useful in the foamable compositions of the present invention are substances that soften and soothe the skin.

The foamable composition of the present invention can include an occlusive agent. The occlusive agent of the foamable compositions of the present invention can be any excipient or combination thereof that provides an occlusive layer or hydration barrier to the skin. An occlusive layer or hydration barrier is a layer or barrier sufficient to result in reduction in trans epidermal water loss, which results in skin hydration. The occlusive agent in the foamable compositions of the present invention is selected from the group consisting of a mineral oil, grease, petrolatum, an animal fat, a vegetable fat, a water insoluble polymer, a fatty alcohol, and mixtures thereof. In one embodiment, the occlusive agent is white petrolatum. In another embodiment, the occlusive agent is a fatty alcohol, or combination of fatty alcohols, as described above. In a further embodiment, the occlusive agent is a mixture of white petrolatum and a fatty alcohol or combination of fatty alcohols. In other embodiments, the occlusive agent is a mixture of white petrolatum and light mineral oil. One of skill in the art will appreciate that further occlusive agents are useful in the present invention.

Other occlusive agents useful in the present invention include hydrophobic solvents such as mineral oil. Mineral oil (Chemical Abstracts Service Registry number 8012-95-1) is a mixture of aliphatic, naphthalenic, and aromatic liquid hydrocarbons that are derived from petroleum. It is typically liquid; its viscosity is in the range of about 35 CST to about 100 CST (at 40° C.), and its pour point (the lowest temperature at which an oil can be handled without excessive amounts of wax crystals forming) is below 0° C.

Other occlusive agents are liquid oils from vegetable, marine or animal sources. By way of example, the unsaturated oil may be selected from the group consisting of olive, corn, soybean, canola, cottonseed, coconut, sesame, sunflower, borage seed, syzigium aromaticum, hempseed, herring, cod-liver, salmon, flaxseed, wheat germ and evening primrose oils and mixtures thereof, at any proportion.

Another class of oils suitable for use as the occlusive agent is liquid hydrophobic plant-derived oils, or essential oils, e.g. "therapeutic oils" containing active biologically occurring molecules that have a therapeutic effect when applied topically. Examples of such oils include rosehip oil, which contain retinoids and is known to reduce acne and post-acne scars, and tea tree oil, which possess antibacterial, antifungal and antiviral properties. Other examples of essential oils are oils of basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil, know in the art of herbal medication.

In one or more embodiments of the present invention, the occlusive agent comprises silicone oil. Silicone oils are used in the foamable compositions due to their known skin protective and occlusive properties.

Suitable silicone oils for use in the invention include non-volatile silicones, such as polyalkyl siloxane, polyaryl siloxane, polyalkylaryl siloxanes and polyether siloxane copolymers, polydimethylsiloxanes (dimethicones) and poly(dimethylsiloxane)-(diphenyl-siloxane) copolymers. These are preferably chosen from cyclic or linear polydimethylsiloxanes containing from about 3 to about 9, preferably from about 4 to about 5, silicon atoms. Volatile silicones such as cyclomethicones can also be used. Water-soluble silicones, such as dimethicone copolyol are not included in the definition of silicone oils (as occlusive agents) according to the present invention.

Additional examples of suitable emollients for use in the present invention include isostearic acid derivatives, isopropyl palmitate, lanolin oil, diisopropyl dimerate, diisopropyl adipate, dimethyl isosorbide, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated cocoglycerides, isononyl isononanoate, isotridecyl isononanoate, myristyl myristate, triisocetyl citrate, octyl dodecanol, octyl hydroxystearate and mixtures thereof. Other examples of other suitable emollients can also be found in the Cosmetic Bench Reference, pp. 1.19-1.22 (1996).

In one or more embodiments of the present invention, the composition comprises at least 2% (w/w foamable composition) silicone oil, alone or as part of the occlusive agent. Yet, in other embodiments, the composition comprises at least 5% (w/w) silicone oil alone or as part of the occlusive agent.

The occlusive agent can be present in an amount sufficient to permit the formation of an occlusive layer or hydration barrier on the skin of the patient. In one embodiment, the amount of occlusive agent present in the foamable composition of the present invention is from about 0.1% to approximately 55% by weight, based on the total weight of the foamable composition. In another embodiment, the amount of occlusive agent is present in an amount of from about 0.1% to about 25% by weight. In a further embodiment, the occlusive agent is present in an amount of from about 0.1% to about 10% by weight, based on the total weight of the foamable composition. One of skill in the art will appreciate that other amounts of the occlusive agent are useful in the present invention.

Humectants useful in the foamable composition of the present invention include, but are not limited to, propylene glycol. When a humectant is present, it is present in an amount of from about 1% to about 20% by weight. In some embodiments, the humectant is present in an amount of from about 5% to about 15% by weight. One of skill in the art will appreciate that other humectants, and amounts, are useful in the present invention.

F. Buffering Agent

In certain embodiments, the compositions contain a pH-adjusting agent, for example, an acid, a base, a buffering pair or a buffering agent. In some embodiments, the pH-adjusting agent is a buffering agent, for example, a buffering pair to stably maintain a desired pH. The chosen buffering agent or buffering pair selected will depend on the active ingredients included in the composition.

The buffering agent or pH adjusting agent can be any inorganic or organic acid or base that maintains the pH at a desired point. Buffering agents and/or pH adjusting agents useful in the present invention include, but are not limited to, sodium hydroxide, dibasic sodium phosphate anhydrous, and mixtures thereof. In some embodiments, the agent is sodium hydroxide. In other embodiments, the agent is dibasic sodium phosphate anhydrous. In a further embodiment, the agent is a mixture of sodium hydroxide and dibasic sodium phosphate anhydrous. One of skill in the art will appreciate that other buffering agents or pH adjusting agents are useful in the present invention.

In another embodiment, the pH of the foamable composition is from about pH 4.0 to about pH 9.0 (e.g., pH 4.0, 5.0, 6.0, 7.0, 8.0 or 9.0 and pH values in-between). In other embodiments, the pH is from about pH 7.0 to about pH 9.0. One of skill in the art will appreciate that other pHs of the foamable compositions are useful in the present invention.

In some embodiments, the desired pH is an acidic pH. Exemplified buffering agents to maintain an acidic pH include, for example, citric acid/citrate, acetic acid/acetate, BICINE, HEPES, Trizma. In some embodiments, the desired pH is a neutral pH. Exemplified buffering agents to maintain a neutral pH include HEPES, TRIS, phosphoric acid/phosphate, Trizma. In some embodiments, the desired pH is a basic pH. Exemplified buffering agents to maintain a basic pH include TRIS, Trizma, HEPES, carbonate/bicarbonate. These and additional biological buffers are available from Sigma-Aldrich, St. Louis, Mo. or Merck, Darmstadt, Germany. The buffering agent can also be an amino acid, for example, glycine, histidine, arginine, lysine, asparagine, aspartic acid, glutamine, glutamic acid. In certain instances, it may be appropriate to add an acid or a base, for example, HCl, NaOH, KOH to arrive at the proper pH value.

The buffering agent or buffering pair can be included at a concentration of up to about 1%, usually up to about 0.3%, 0.5%, 0.7%, or in a range of about 0.1-1.0%, 0.3-0.8%. The foamable compositions can contain about 0.1, 0.2, 0.3, 0.4, 0.5, 0.6, 0.8, 0.9, 1.0% (w/w) of a buffering agent or a buffering pair.

When a buffering agent or pH adjusting agent is present, it is present in an amount of about 0.001% to about 1.0% by weight. One of skill in the art will appreciate that other amounts of buffering agent or pH adjusting agent are useful in the present invention.

G. Additional Pharmaceutical Excipients

The foamable compositions of the present invention can also comprise additional adjuvants, such as a viscosity reducer, a complexing agent, a gelling agent, an antioxidant, a thickener, a preservative, a corrosion inhibitor, a penetration enhancer, colors and fragrances.

Viscosity reducers useful in the foamable composition of the present invention include, but are not limited to, isopropyl myristate, light mineral oil and cyclomethicone and mixtures thereof. In one embodiment, the foamable composition of the present invention comprises a mixture of isopropyl myristate, light mineral oil and cyclomethicone as a viscosity reducer. When a viscosity reducer is present, it is present in an amount of about 1% to about 20% by weight. One of skill in the art will appreciate that other viscosity reducers, and amounts, are useful in the present invention.

Complexing agents useful in the foamable composition of the present invention include, but are not limited to, edetate disodium dehydrate. When a complexing agent is present, it is present in an amount of from about 0.001% to about 1%. One of skill in the art will appreciate that other complexing agents, and amounts, are useful in the present invention.

Gelling agents useful in the foamable composition of the present invention include, but are not limited to, amphiphilic copolymers. Amphiphilic copolymers include polymers having hydrophobic groups and hydrophilic groups or regions. These materials are referred to alternatively as "polymeric surfactants" because the hydrophilic and hydrophobic regions of the polymers serve to interact with and stabilize hydrophilic and lipophilic components, respectively, of a composition. The copolymer may be a random copolymer, a block copolymer or a graft copolymer. Exemplary amphiphilic copolymers include di-, tri- or multi-block copolymer or graft copolymer of a biodegradable polymer.

The polymeric surfactant gelling agents may be an acrylate cross polymer. By way of example, suitable polymeric surfactants include cross linked copolymers of acrylic acid and a hydrophobic comonomer, such as Pemulen TR-1 and Pemulen TR-2, ETD 2020 and Carbopol 1382 (all, Acrylates/C10-30 alkyl acrylate crosspolymer), Natrosol CS Plus 330 and 430 and Polysurf 67 (all, cetyl hydroxyethyl cellulose), Aculyn 22 (acrylates/steareth-20 methacrylate copolymer), Aculyn 25 (acrylates/laureth-25 methacrylate copolymer), Aculyn 28 (acrylates/beheneth-25 methacrylate copolymer), Aculyn 46 (PEG-150/stearyl alcohol/SMDI copolymer), Stabylen 30 (acrylates/vinyl isodecanoate), Structure 2001 (acrylates/steareth-20 itaconate copolymer), Structure 3001 (acrylates/ceteth-20 itaconate copolymer) and Structure Plus (acrylates/aminoacrylates/C10-30 alkyl PEG 20 itaconate copolymer), where PEG is polyethylene glycol, PPG is polypropylene glycol.

Other exemplary amphiphilic copolymers include silicone polymers such as amphiphilic silicone polyols or copolyol, for example cetyl dimethicone copolyol and dimethicone copolyol PPG-3 oleyl ether, acetylated starch derivatives, amphiphilic modified starches, and amphiphilic block copolymers of ethylene oxide and propylene oxide (also known as "poloxamer").

Other exemplary gelling agents include locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Optionally, mixtures of the above compounds are contemplated.

The gelling agent can be present in the foamable composition in an amount of about 0.1 to 5.0 wt % by weight. The gelling agent included in the foamable composition can be less than 1 wt % by weight of the foamable composition.

An antioxidant useful in the present invention is one that retards oxidation and subsequent deterioration of the pharmaceutically active agent. Examples of antioxidants useful in the compositions of the present invention include, but are not limited to, beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, 1-carnitine, phenoxyethanol, butylated hydroxytoluene and sodium benzoate. Antioxidants are also known as preservatives. When a preservative or antioxidant is present, it is present in an amount of from about 0.01% to about 5% by weight. One of skill in the art will appreciate that other preservatives and antioxidants, and amounts, are useful in the present invention.

In some instances, a penetration enhancer or permeation enhancer is useful in the foamable compositions of the present invention. A penetration enhancer or permeation enhancer is an agent used to increase the permeability of the skin to a pharmaceutically active agent to increase the rate at which the drug diffuses through the skin and enters the tissues and bloodstream. A chemical skin penetration enhancer increases skin permeability by reversibly altering the physiochemical nature of the stratum corneum to reduce its diffusional resistance.

Examples of penetration enhancers, according to the present invention include: polyols, such as propyleneglycol, hexylene glycol, diethylene glycol, propylene glycol n-alkanols, terpenes, di-terpenes, tri-terpenes, terpen-ols, limonen, terpene-ol, 1-menthol, dioxolane, ethylene glycol, other glycols, and glycerol; sulfoxides, such as dimethylsulfoxide (DMSO), dimethylformamide, methyl dodecyl sulfoxide, dimethyl acetamide; monooleate of ethoxylated glycerides (with 8 to 10 ethylene oxide units); Azone (1-dodecylazacycloheptan-2-one), 2-(n-nonyl)-1,3-dioxolane; esters, such as isopropyl myristate/palmitate, ethyl acetate, butyl acetate, methyl propionate, capric/caprylic triglycerides, octylmyristate, dodecyl-myristate; myristyl alcohol, lauryl alcohol, lauric acid, lauryl lactate ketones; amides, such as acetamide oleates such as triolein; various surfactants, such as sodium lauryl sulfate; various alkanoic acids such as caprylic acid; lactam compounds, such as azone; alkanols, such as oleyl alcohol; dialkylamino acetates, and admixtures thereof.

Yet another preferred class of penetration enhancers is the cyclodextrins and related compounds. Cyclodextrins are structurally related cyclic oligomaltoses which form a new group of pharmaceutical excipients. These are torus-shaped molecules with a hydrophilic outer surface and a lipophilic central cavity. Cyclodextrins are capable of forming water-soluble inclusion complexes with a wide variety of lipophilic water-insoluble drugs by taking up a whole drug molecule, or some part of it, into the cavity. The cyclodextrin molecules are relatively large (molecular weight ranging from almost 1000 to over 1500), with a hydrated outer surface, and under normal conditions, cyclodextrin molecules will only permeate the skin barrier with considerable difficulty. It is generally believed that the cyclodextrin molecules act as true carriers by keeping lipophilic drug molecules in solution and deliver them to the skin surface where they partition from the cyclodextrin cavity into the skin.

In some embodiments, the compositions of the present invention include a thickener. A thickener increases viscosity without substantially modifying other properties of a composition to which it is added. Thickeners provide body, increase stability, and improve suspending action. Thickeners useful in the compositions of the instant invention include, but are not limited to, agar, alginin, arrowroot, collagen, cornstarch, fecula, gelatin, guar gum, katakuri, locust bean gum, pectin, roux, tapioca, and xanthan gum. One of skill in the art will appreciate that other thickeners are useful in the present invention.

According to an embodiment of the invention, where the pharmaceutically active agent is an immune response modifier compound, the compositions can further include a corticosteroid such as those set forth in U.S. Pat. No. 6,126,920, which is incorporated herein by reference. Suitable corticosteroids include, for example, alclometasone dipropionate, fluclorolone acetonide, amcinonide, fluocinolone acetonide, beclamethasone dipropionate, fluocinonide, betamethasone benzoate, fluocortin butyl, betamethasone dipropionate, fluocortolone preparations, betamethasone valerate, fluprednidene acetate, budesonide, flurandrenolone, clobetasol propionate, halcinonide, clobetasone butyrate, hydrocortisone, desonide, hydrocortisone acetate, desoxymethasone, hydrocortisone butyrate, diflorasone diacetate, methylprednisolone acetate, diflucortolone valerate, mometasone furoate, flumethasone pivalate, triamcinolone acetonide, and pharmacologically effective mixtures thereof.

H. Aerosol Propellants

The foamable compositions of the present invention can also comprise an effective amount of an aerosol propellant. The aerosol propellant can be any suitable gas or mixture thereof, such as a hydrocarbon, a chlorofluorocarbon, dimethyl ether, hydrofluorocarbons and a mixture thereof. Additional foamable compositions can comprise an aerosol propellant such as nitrogen or air. In one embodiment, the aerosol propellant is a mixture of hydrocarbons. In another embodiment, the aerosol propellant is a mixture of propane, n-butane and isobutane. When such a mixture of hydrocarbon gasses is used as the aerosol propellant, the propane can be present in an amount of from about 10% to about 90% of the propellant mixture. In other embodiments, the propane can be present in an amount of from about 40% to about 70%. The n-butane used in such a mixture can be present in an amount from about 5% to about 50%. In another embodiment, the n-butane can be present in an amount from about 20% to about 40%. The isobutane used in such a mixture can be present in an amount from about 1% to about 30%. In some embodiments, the isobutane can be present in an amount from about 10% to about 20%. One of skill in the art will appreciate that other combinations of propellant are useful in the present invention.

The aerosol propellant can be present in the foamable composition in an amount of from approximately 2.5% to 20% by weight of the foamable composition, or 5% to 15% by weight. In some embodiments, the aerosol propellant is present in an amount from about 5% to 10% by weight, such as 5%, 6%, 7%, 8%, 9% or 10% by weight. The propellant may be introduced into the foamable composition at the time of filling utilizing a pressurized container such as a standard aerosol dispenser. One of skill in the art will appreciate that other aerosol amounts are useful in the present invention.

When the foamable composition is released from the pressurized container, the foamable composition is a foam. Preferably, the foam breaks easily with shear. More preferably, the foam is homogenous.

A preferred composition of the present invention includes imiquimod as the immune response modifier compound in an amount of about 0.001% to 10% by weight, a $C_{18}$ fatty acid as the organic solvent in an amount of from about 10% to about 50% by weight. A base in an amount from about 0.01% to about 30% by weight, and water in an amount of about 45% to about 90% by weight. One of skill in the art will appreciate that other foamable compositions of the present invention are comprised of different components or in different amounts.

III. Methods of Treatment

The present invention includes a method for treating a dermatological disorder in a mammal, the method comprising the step of administering a foamable composition of the invention to treat the dermatological disorder.

Dermatological disorders that are treatable by the methods of the present invention include, but are not limited to, dermatological conditions linked to disorders of keratinization involving differentiation and proliferation, in particular, acne vulgaris, comedonic or polymorphic acne, nodulocystic acne, acne conglobata, senile acne and secondary acnes such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis. Other disorders treatable by the methods of the present invention include precancerous lesions such as actinic keratosis, melanoma and nonmelanoma skin cancers (such as basal cell carcinoma), and warts (such as external genital warts). The present invention contemplates the treatment of skin disorders of humans and animals. In one embodiment, the dermatological disorder treated by the methods of the present invention is psoriasis or atopic dermatitis. In another embodiment, the dermatological disorder treated is actinic keratosis, basal cell carcinoma or external genital warts. One of skill in the art will appreciate that other dermatological disorders are useful in the present invention.

The foamable compositions useful in the methods of the present invention are described above. Preferably, the foamable composition is administered topically.

The following examples are provided by way of illustration only and not by way of limitation. Those of skill in the art will readily recognize a variety of non-critical parameters that can be changed or modified to yield essentially similar results.

IV. Examples—Rheological Characterization & Method of Manufacture

The following worked examples are provided so as to illustrate, but not limit, the scope of the present invention.

Example 1

The physical stability of aerosol foam is influenced by the cohesive forces that exist between the aerosol base (i.e. the foamable composition) and the aerosol propellant (i.e. the foaming agent). Thus, the rheological characterization of a foam structure is relevant in determining whether foam will persist or break easily with shear. For example, in order for foam to persist the foam structure requires sufficient viscosity at near zero shear rates to exhibit this behavior. Similarly, the yield stress required to deform the foam structure provides an indication of the foam's ability to maintain the physical structure during the application of shear forces. Also, subjecting foam to constant shear will provide a measure of the foam's ability to retain its structure.

In order to understand the behavior of foam and the boundary between persistent foam and foam that breaks easily with shear it is worthwhile to compare observations with rheology data for a range of foam products. Accordingly, various foam samples were assessed topically and the observations were recorded as either (i) foam persists, or, (ii) foam breaks easily with shear. A rheological characterization of these foam samples was conducted using a programmable Rheometer whilst maintaining a constant temperature of 20° C. (Brookfield RIS-CPS Rheometer with Peltier Thermo Regulator PTR-I). Foam samples were assessed using a three-step process; Step 1—the shear rate is increased from 10 to 100 ($s^{-1}$) over a 60 second period, Step 2—the shear rate of 100 ($s^{-1}$) is maintained for 10 seconds, and, Step 3—the shear rate is decreased from 100 to 10 ($s^{-1}$) over a 60 second period. The Yield Stress is calculated in Step 1, the Average Viscosity is determined during Step 2 and the Change in Viscosity is determined by the difference between the Initial Viscosity (Start of Step 1) and the Final Viscosity (End of Step 3). Finally, the product of |Yield Stress|×|Average Viscosity|×|Change in Viscosity| has been assigned as the Foam Stability Value (FSV) in order to obtain a numerical result that is relevant to describe the foam's stability. The data from the rheological characterization is presented below in Table 1, and in FIG. 1.

TABLE 1

| Sample Details | Batch Details | Initial Viscosity [Pas] | Yield Stress [Pa] | Average Viscosity [Pas] | Final Viscosity [Pas] | Change in Viscosity [Pas] | Foam Stability Value | Observations [Following topical application] |
|---|---|---|---|---|---|---|---|---|
| Gillette Foam | 6305051852 | 5.09 | 41.47 | 1.26 | 4.13 | 0.96 | 49.90 | Foam persists |
| Rapid Shave | 14456 | 5.19 | 41.77 | 1.27 | 4.32 | 0.87 | 46.47 | Foam persists |
| Hydroethanolic Foam | D4G043-2 | 3.83 | 34.74 | 0.55 | 2.72 | 1.11 | 21.37 | Foam breaks easily with shear |
| Emulsion Foam | D6H109-2 | 1.32 | 9.73 | 0.23 | 0.74 | 0.58 | 1.26 | Foam breaks easily with shear |

The data in Table 1 and FIG. 1 demonstrate the differences between persistent foam and foam that breaks easily with shear. In particular, it is interesting to note that the foams that break easily with shear have a relatively low average viscosity when compared to (i) the initial and final viscosities and (ii) the average viscosity of persistent foams. This aspect is consistent with the understanding of foam structure disruption and the reduced cohesion of foam that breaks easily with shear. Therefore, considering the FSV for samples of persistent foam, it appears that a foam that breaks easily with shear must have an FSV of less than approximately 45 to 50.

Example 2

TABLE 2

| | OLEIC ACID + TRIETHANOLAMINE 10 to 60% Neutralization | | | | | | |
|---|---|---|---|---|---|---|---|
| | | Batch # | | | | | |
| Ingredient | Function | 645-07-01 % w/w | 645-07-02 % w/w | 645-07-03 % w/w | 645-07-04 % w/w | 645-07-05 % w/w | 645-07-06 % w/w |
| | AEROSOL BASE | | | | | | |
| Oleic acid | Organic solvent, Liquid fatty acid | 14.12 | 14.12 | 14.12 | 14.12 | 14.12 | 14.12 |

TABLE 2-continued

OLEIC ACID + TRIETHANOLAMINE 10 to 60% Neutralization

| Ingredient | Function | 645-07-01 % w/w | 645-07-02 % w/w | 645-07-03 % w/w | 645-07-04 % w/w | 645-07-05 % w/w | 645-07-06 % w/w |
|---|---|---|---|---|---|---|---|
| Triethanolamine | Base, Neutralizing agent | 0.746 | 1.492 | 2.238 | 2.984 | 3.73 | 4.476 |
| Purified water | Solvent, Diluent | 85.134 | 84.388 | 83.642 | 82.896 | 82.15 | 81.404 |
| TOTAL | | 100.00 | 100.00 | 100.00 | 100.00 | 100.00 | 100.00 |
| % Neutralization | | 10 | 20 | 30 | 40 | 50 | 60 |
| AEROSOL BASE + PROPELLANT | | | | | | | |
| AEROSOL BASE | | 90 | 90 | 90 | 90 | 90 | 90 |
| Hydrocarbon Propellant AP70 | Propellant | 10 | 10 | 10 | 10 | 10 | 10 |
| TOTAL | | 100.00 | 100.00 | 100.00 | 100.00 | 100.00 | 100.00 |

Method of Manufacture:
1. Add Oleic acid to the main mixing vessel.
2. Add Triethanolamine to the main mixing vessel and commence stirring.
3. Warm contents of main mixing vessel to approximately 50° C. whilst stirring.
4. In a separate vessel add Purified water and commence heating to approximately 50° C.
5. Whilst stirring the contents of the main mixing vessel (@~50° C.), slowly add the Purified water (also @~50° C.).
6. Continue mixing the contents of the main mixing vessel until the contents are uniform.
7. Cool the contents of the main mixing vessel to room temperature whilst stirring.
8. Add the Aerosol Base to an aerosol container.
9. Secure a valve onto the aerosol container.
10. Add Propellant to the aerosol container.
11. Shake the aerosol container and dispense the foam.

The foams shown in FIG. 2A are dispensed from each sample of partially-neutralized fatty acid foam. The static stability of the foams improves as the neutralization of fatty acid is increased. Foams that have been partially-neutralized to 50% or more persist, whereas foams that have been neutralized below 50% break easily with shear.

Example 3

TABLE 5

OLEIC ACID + IMIQUIMOD + TRIETHANOLAMINE

| Ingredient | Function | 651-04-02 % w/w | 651-04-03 % w/w | 651-04-04 % w/w | 651-04-05 % w/w | 651-04-06 % w/w | 651-04-07 % w/w |
|---|---|---|---|---|---|---|---|
| AEROSOL BASE | | | | | | | |
| Oleic acid | Organic solvent, Liquid fatty acid | 30.00 | 30.00 | 30.00 | 30.00 | 30.00 | 30.00 |
| Imiquimod | Active ingredient | 5.00 | 5.00 | 5.00 | 5.00 | 5.00 | 5.00 |
| Triethanolamine | Base, Neutralizing agent | 0.50 | 1.00 | 1.50 | 2.00 | 2.50 | 3.00 |
| Purified water | Solvent, Diluent | 64.50 | 64.00 | 63.50 | 63.00 | 62.50 | 62.00 |
| TOTAL | | 100.00 | 100.00 | 100.00 | 100.00 | 100.00 | 100.00 |
| % Neutralization | | 22.7 | 25.9 | 29.1 | 32.2 | 35.4 | 38.5 |
| AEROSOL BASE + PROPELLANT | | | | | | | |
| AEROSOL BASE | | 90 | 90 | 90 | 90 | 90 | 90 |
| Hydrocarbon Propellant AP70 | Propellant | 10 | 10 | 10 | 10 | 10 | 10 |
| TOTAL | | 100.00 | 100.00 | 100.00 | 100.00 | 100.00 | 100.00 |

Method of Manufacture:
1. Add Oleic acid to the main mixing vessel.
2. Add Imiquimod to the main mixing vessel.
3. Add Triethanolamine to the main mixing vessel and commence stirring.
4. Warm contents of main mixing vessel to approximately 75° C. whilst stirring.
5. In a separate vessel add Purified water and commence heating to approximately 75° C.
6. Whilst stirring the contents of the main mixing vessel (@~75° C.), slowly add the Purified water (also @~75° C.).
7. Continue mixing the contents of the main mixing vessel until the contents are uniform.
8. Cool the contents of the main mixing vessel to room temperature whilst stirring.
9. Add the Aerosol Base to an aerosol container.
10. Secure a valve onto the aerosol container.
11. Add Propellant to the aerosol container.
12. Shake the aerosol container and dispense the foam.

The foams shown in FIG. 3A have an active ingredient (e.g. Imiquimod) added to the fatty acid solvent. This addition does not inhibit the production of foam from the partially-neutralized fatty acid foam. The static stability of partially-neutralized fatty acid foam that contains an active ingredient (e.g. Imiquimod) improves as the neutralization of the fatty acid solvent is increased. The active ingredient (e.g. Imiquimod) can contribute to the neutralization of the fatty acid solvent. Partially-neutralized fatty acid foams that contain an active ingredient (e.g. Imiquimod) can persist when neutralized beyond approximately 35%, whereas those neutralized below approximately 35% break easily with shear.

Example 4

TABLE 8

ISOSTEARIC ACID + TRIETHANOLAMINE 30 to 40% Neutralization

| Ingredient | Function | Batch # | | |
| --- | --- | --- | --- | --- |
| | | 651-08-04 % w/w | 651-08-05 % w/w | 651-08-06 % w/w |
| Isostearic acid | Organic solvent, Liquid fatty acid | 15.00 | 15.00 | 15.00 |
| Triethanolamine | Base, Neutralizing agent | 2.35 | 2.75 | 3.15 |
| Purified water | Solvent, Diluent | 72.65 | 72.25 | 71.85 |
| Hydrocarbon Propellant AP70 | Propellant | 10.0 | 10.00 | 10.00 |
| TOTAL | | 100.00 | 100.00 | 100.00 |
| % Neutralization | | 30 | 35 | 40 |

Method of Manufacture:

1. Add Isostearic acid to the main mixing vessel.
2. Add Triethanolamine to the main mixing vessel and commence stirring.
3. Warm contents of main mixing vessel to approximately 50° C. whilst stirring.
4. In a separate vessel add Purified water and commence heating to approximately 50° C.
5. Whilst stirring the contents of the main mixing vessel (@~50° C.), slowly add the Purified water (also @~50° C.).
6. Continue mixing the contents of the main mixing vessel until the contents are uniform.
7. Cool the contents of the main mixing vessel to room temperature whilst stirring.
8. Add the Aerosol Base to an aerosol container.
9. Secure a valve onto the aerosol container.
10. Add Propellant to the aerosol container.
11. Shake the aerosol container and dispense the foam.

TABLE 9

FOAM STABILITY—RHEOLOGICAL CHARACTERISATION (@20° C.)

| Batch # | % Neutralization | Initial Viscosity [Pas] | Average Viscosity [Pas] | Final Viscosity [Pas] | Yield Stress [Pa] | Viscosity Change [Pas] | Foam Stability Value (FSV) |
| --- | --- | --- | --- | --- | --- | --- | --- |
| 651-08-04 | 30 | 2.434 | 0.672 | 2.200 | 19.999 | 0.234 | 4.433 |
| 651-08-05 | 35 | 6.095 | 0.016 | 0.066 | 76.179 | 6.029 | 7.300 |
| 651-08-06 | 40 | 8.955 | 0.726 | 0.550 | 84.674 | 8.405 | 510.542 |

Observations & Conclusions
1. Foam is dispensed from each sample of partially-neutralized fatty acid foam.
2. The static stability of foams improves as the neutralization of fatty acid is increased.
3. Foams that have been partially-neutralized to 40% or more persist, whereas foams that have been neutralized below 40% break easily with shear.

Example 5

TABLE 10

| LINOLEIC ACID + TRIETHANOLAMINE 30 to 40% Neutralization | | | | | | | |
|---|---|---|---|---|---|---|---|
| | | Batch # | | | | | |
| | | 651-10-01 | 651-10-02 | 651-10-03 | 651-10-04 | 651-10-05 | 651-10-06 |
| | | AEROSOL BASE + PROPELLANT | | | | | |
| Ingredient | Function | % w/w | % w/w | % w/w | % w/w | % w/w | % w/w |
| Linoleic acid | Organic solvent, Liquid fatty acid | 30.00 | 30.00 | 30.00 | 15.00 | 15.00 | 15.00 |
| Triethanolamine | Base, Neutralizing agent | 4.80 | 5.60 | 6.40 | 2.40 | 2.80 | 3.20 |
| Purified water | Solvent, Diluent | 55.20 | 54.40 | 53.60 | 72.60 | 72.20 | 71.80 |
| Hydrocarbon Propellant AP70 | Propellant | 10.00 | 10.00 | 10.00 | 10.0 | 10.00 | 10.00 |
| TOTAL | | 100.00 | 100.00 | 100.00 | 100.00 | 100.00 | 100.00 |
| % Neutralization | | 30 | 35 | 40 | 30 | 35 | 40 |

Method of Manufacture:
1. Add Linoleic acid to the main mixing vessel.
2. Add Triethanolamine to the main mixing vessel and commence stirring.
3. Warm contents of main mixing vessel to approximately 50° C. whilst stirring.
4. In a separate vessel add Purified water and commence heating to approximately 50° C.
5. Whilst stirring the contents of the main mixing vessel (@~50° C.), slowly add the Purified water (also @~50° C.).
6. Continue mixing the contents of the main mixing vessel until the contents are uniform.
7. Cool the contents of the main mixing vessel to room temperature whilst stirring.
8. Add the Aerosol Base to an aerosol container.
9. Secure a valve onto the aerosol container.
10. Add Propellant to the aerosol container.
11. Shake the aerosol container and dispense the foam.

Observations & Conclusions
1. Foam is dispensed from each sample of partially-neutralized fatty acid foam.
2. The static stability of foams improves as the neutralization of fatty acid is increased.
3. Foams that have been partially-neutralized to 40% or more persist, whereas foams that have been neutralized below 40% break easily with shear.

Example 6

TABLE 11

| CAPRIC ACID + TRIETHANOLAMINE 30 to 40% Neutralization | | | | |
|---|---|---|---|---|
| | | Batch # | | |
| | | 651-11-01 | 651-11-04 | 651-11-06 |
| Ingredient | Function | % w/w | % w/w | % w/w |
| Capric acid | Organic solvent, Liquid fatty acid | 30.00 | 15.00 | 15.00 |
| Triethanolamine | Base, Neutralizing agent | 7.80 | 3.90 | 5.70 |
| Purified water | Solvent, Diluent | 52.20 | 71.10 | 69.30 |
| Hydrocarbon Propellant AP70 | Propellant | 10.00 | 10.0 | 10.00 |
| TOTAL | | 100.00 | 100.00 | 100.00 |
| % Neutralization | | 30 | 30 | 40 |

Method of Manufacture:
1. Add Capric acid to the main mixing vessel.
2. Add Triethanolamine to the main mixing vessel and commence stirring.
3. Warm contents of main mixing vessel to approximately 50° C. whilst stirring.

4. In a separate vessel add Purified water and commence heating to approximately 50° C.
5. Whilst stirring the contents of the main mixing vessel (@~50° C.), slowly add the Purified water (also @~50° C.).
6. Continue mixing the contents of the main mixing vessel until the contents are uniform.
7. Cool the contents of the main mixing vessel to room temperature whilst stirring.
8. Add the Aerosol Base to an aerosol container.
9. Secure a valve onto the aerosol container.
10. Add Propellant to the aerosol container.
11. Shake the aerosol container and dispense the foam.

TABLE 12

FOAM STABILITY—RHEOLOGICAL CHARACTERISATION (@20° C.)

| Batch # | % Neutralization | Initial Viscosity [Pas] | Average Viscosity [Pas] | Final Viscosity [Pas] | Yield Stress [Pa] | Viscosity Change [Pas] | Foam Stability Value (FSV) |
|---|---|---|---|---|---|---|---|
| 651-11-01 | 30 | 5.777 | 0.000 | 0.285 | 61.136 | 5.492 | 0.000 |
| 651-11-04 | 30 | 5.111 | 0.041 | 0.236 | 59.359 | 4.875 | 11.734 |
| 651-11-06 | 40 | 5.166 | 0.431 | 2.016 | 53.385 | 3.151 | 72.079 |

Observations & Conclusions
1. Foam is dispensed from each sample of partially-neutralized fatty acid foam.
2. The static stability of foams improves as the neutralization of fatty acid is increased.
3. Foams that have been partially-neutralized to 40% or more persist, whereas foams that have been neutralized below 40% break easily with shear.

Example 7

TABLE 13

NEUTRALIZATION OF FATTY ACID WITH ACTIVE INGREDIENT ONLY—MINOXIDIL AND IMIQUIMOD (NO TRIETHANOLAMINE)

| | | Batch # | | | | | |
|---|---|---|---|---|---|---|---|
| | | 645-10-01 | 645-03-06 | 651-02-01 | 651-02-02 | 651-02-03 | 651-02-04 |
| | | AEROSOL BASE + PROPELLANT | | | | | |
| Ingredient | Function | % w/w | % w/w | % w/w | % w/w | % w/w | % w/w |
| Oleic acid | Organic solvent, Liquid fatty acid | 30.00 | 25.00 | 0 | 0 | 0 | 0 |
| Linoleic acid | Organic solvent, Liquid fatty acid | 0 | 0 | 30.00 | 30.00 | 30.00 | 30.00 |
| Stearic Acid | Solid fatty acid | 0 | 0 | 3.00 | 4.00 | 5.00 | 6.00 |
| Isopropyl myristate | Organic solvent, Emollient | 0 | 5.00 | 0 | 0 | 0 | 0 |
| Petrolatum | Occlusive agent, Emollient | 0 | 3.00 | 0 | 0 | 0 | 0 |
| Cetyl Alcohol | Viscosity Increasing Agent—Nonaqueous, Emollient | 0 | 5.00 | 0 | 0 | 0 | 0 |
| Minoxidil | Active Ingredient, Neutralizing agent | 5.00 | 0 | 0 | 0 | 0 | 0 |
| Imiquimod | Active Ingredient, Neutralizing agent | 0 | 5.00 | 5.00 | 5.00 | 5.00 | 5.00 |
| Benzyl Alcohol | Preservative | 4.00 | 2.00 | 0 | 0 | 0 | 0 |

TABLE 13-continued

NEUTRALIZATION OF FATTY ACID WITH ACTIVE INGREDIENT ONLY—MINOXIDIL AND IMIQUIMOD (NO TRIETHANOLAMINE)

| Ingredient | Function | Batch # 645-10-01 % w/w | Batch # 645-03-06 % w/w | Batch # 651-02-01 % w/w | Batch # 651-02-02 % w/w | Batch # 651-02-03 % w/w | Batch # 651-02-04 % w/w |
|---|---|---|---|---|---|---|---|
| | | AEROSOL BASE + PROPELLANT | | | | | |
| Purified water | Solvent, Diluent | 51.00 | 45.00 | 52.00 | 51.00 | 50.00 | 49.00 |
| Hydrocarbon Propellant AP70 | Propellant | 10.00 | 10.00 | 10.00 | 10.00 | 10.00 | 10.00 |
| TOTAL | | 100.00 | 100.00 | 100.00 | 100.00 | 100.00 | 100.00 |
| % Neutralization (of all fatty acids) | | 22.5 | 23.5 | 17.8 | 17.3 | 16.8 | 16.3 |

Method of Manufacture:
1. Add Fatty acid(s) acid to the main mixing vessel.
2. Add Emollient(s) to the main mixing vessel and commence stirring.
3. Warm contents of main mixing vessel to approximately 75° C. whilst stirring.
4. Add Active Ingredient to the main mixing vessel and continue stirring the contents at 75° C.
5. In a separate vessel add Purified water and commence heating to approximately 75° C.
6. Whilst stirring the contents of the main mixing vessel (@~75° C.), slowly add the Purified water (also @~75° C.).
7. Add Preservative(s) to the main mixing vessel and continue stirring.
8. Continue mixing the contents of the main mixing vessel until the contents are uniform.
9. Cool the contents of the main mixing vessel to room temperature whilst stirring.
10. Add the Aerosol Base to an aerosol container.
11. Secure a valve onto the aerosol container.
12. Add Propellant to the aerosol container.
13. Shake the aerosol container and dispense the foam.

Foam Stability—Rheological Characterisation (@20° C.)

| Batch # | % Neutralization | Initial Viscosity [Pas] | Average Viscosity [Pas] | Final Viscosity [Pas] | Yield Stress [Pa] | Viscosity Change [Pas] | Foam Stability Value (FSV) |
|---|---|---|---|---|---|---|---|
| 645-10-01 | 22.5 | 0.458 | 0.052 | 0 | 3.374 | 0.458 | 0.080 |
| 645-03-06 | 23.5 | 1.007 | 0.064 | 0.000 | 10.373 | 1.007 | 0.654 |
| 651-02-01 | 17.8 | 0.889 | 0.211 | 0.244 | 6.882 | 0.645 | 0.955 |
| 651-02-02 | 17.3 | 1.055 | 0.294 | 0.803 | 8.597 | 0.253 | 0.612 |
| 651-02-03 | 16.8 | 3.231 | 0.673 | 2.981 | 28.798 | 0.250 | 4.537 |
| 651-02-04 | 16.3 | 10.808 | 1.721 | 7.456 | 99.275 | 3.352 | 571.456 |

Observations & Conclusions
1. Wherein the active ingredient comprises the sole neutralizing agent (i.e. acts as the base), foam was dispensed from each sample of partially-neutralized fatty acid foam.
2. The Foam Stability Value (FSV) increases as the proportion of solid, lipophilic materials are added (e.g. Cetyl alcohol, Stearic acid, etc).
3. Wherein the proportion of solid, lipophilic material(s) (e.g. Cetyl alcohol, Stearic acid) added to the liquid fatty acid solvent exceeds approximately $\frac{1}{5}^{th}$ of the total amount of Liquid fatty acid the foam persists, whereas when this is below approximately $\frac{1}{5}^{th}$ the foam breaks easily with sheer.

Example 8

Neutralization of Fatty Acid with Active Ingredient Only (Lidocaine & Metronidazole)

| Ingredient | Function | Batch # | | | | | |
|---|---|---|---|---|---|---|---|
| | | 651-13-01 % w/w | 651-13-02 % w/w | 651-13-03 % w/w | 651-14-04 % w/w | 651-18-04 % w/w | 651-18-06 % w/w |
| AEROSOL BASE | | | | | | | |
| Oleic acid | Organic solvent, Liquid fatty acid | 30.00 | 30.00 | 30.00 | 27.77 | 5.56 | 5.56 |
| Stearic acid | Solid fatty acid | 0 | 0 | 0 | 5.56 | 0 | 5.56 |
| Caprylic/Capric Glycerides | Organic solvent, Emollient | 0 | 0 | 0 | 11.11 | 0 | 22.22 |
| Lidocaine | Active Ingredient, Neutralizing agent | 5.00 | 5.00 | 5.00 | 5.56 | 0 | 0 |
| Metronidazole | Active Ingredient, Neutralizing agent | 0 | 0 | 0 | 0 | 1.11 | 1.11 |
| Glycerin | Humectant | 0 | 0 | 0 | 0 | 22.22 | 0 |
| Purified water | Solvent, Diluent | 65.00 | 65.00 | 65.00 | 50.00 | 71.11 | 65.55 |
| TOTAL | | 100.00 | 100.00 | 100.00 | 100.00 | 100.00 | 100.00 |
| AEROSOL BASE + PROPELLANT | | | | | | | |
| AEROSOL BASE | | 95 | 90 | 80 | 90 | 90 | 90 |
| Hydrocarbon Propellant AP70 | Propellant | 5 | 10 | 20 | 10 | 10 | 10 |
| TOTAL | | 100.00 | 100.00 | 100.00 | 100.00 | 100.00 | 100.00 |
| % Neutralization (of all fatty acids) | | 20.1 | 20.1 | 20.1 | 32.9 | 20.1 | 16.5 |

Observations & Conclusions
1. Wherein the active ingredient comprises the sole neutralizing agent (i.e. acts as the base), foam was dispensed from each sample of partially-neutralized fatty acid foam.
2. The Foam Stability Value (FSV) increases as the proportion of solid, lipophilic materials are added (e.g. Stearic acid).

The following example is provided to further illustrate the subject matter of the present invention.

Example 9. Partially Neutralized Fatty Acid Foams

| Ingredient | Function | 40% Urea Foam % w/w | 1% Ketoconazole Foam % w/w | 0.05% Clobetasol Propionate Foam % w/w | 0.1% Adapalene Foam % w/w | 2.5% Imiquimod + 0.025% Betamethasone Foam % w/w |
|---|---|---|---|---|---|---|
| AEROSOL BASE | | | | | | |
| Oleic acid | Organic solvent, Liquid fatty acid | 14.12 | 0 | 0 | 0 | 30.00 |
| Isostearic acid | Organic solvent, Liquid fatty acid | 0 | 25.00 | 25.00 | 10.00 | 0 |
| Mineral Oil | Organic solvent, Emollient | 0 | 0 | 0 | 15.00 | 0 |
| Imiquimod | Active Ingredient, Neutralizing agent | 0 | 0 | 0 | 0 | 2.50 |

-continued

| Ingredient | Function | 40% Urea Foam % w/w | 1% Ketoconazole Foam % w/w | 0.05% Clobetasol Propionate Foam % w/w | 0.1% Adapalene Foam % w/w | 2.5% Imiquimod + 0.025% Betamethasone Foam % w/w |
|---|---|---|---|---|---|---|
| Ketoconazole | Active Ingredient, Neutralizing agent | 0 | 1.00 | 0 | 0 | 0 |
| Triethanolamine | Base, Neutralizing agent | 2.24 | 5.00 | 1.00 | 1.00 | 2.50 |
| Purified water | Solvent, Diluent | 43.64 | 69.00 | 53.95 | 73.90 | 64.968 |
| Urea | Humectant, Keratolytic agent | 40.00 | 0 | 0 | 0 | 0 |
| Propylene Glycol | Organic solvent, Humectant | 0 | 0 | 20.00 | 0 | 0 |
| Clobetasol Propionate | Active Ingredient | 0 | 0 | 0.05 | 0 | 0 |
| Adapalene | Active Ingredient | 0 | 0 | 0 | 0.1 | 0 |
| Betamethasone dipropionate | Active Ingredient | 0 | 0 | 0 | 0 | 0.0322 |
| TOTAL | | 100.00 | 100.00 | 100.00 | 100.00 | 100.00 |
| AEROSOL BASE + PROPELLANT | | | | | | |
| AEROSOL BASE | | 90 | 90 | 90 | 90 | 90 |
| Hydrocarbon Propellant AP70 | Propellant | 10 | 10 | 10 | 10 | 10 |
| TOTAL | | 100.00 | 100.00 | 100.00 | 100.00 | 100.00 |
| % Neutralization | | 17.0 | 36.5 | 7.6 | 19.1 | 25.8 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for treating a dermatological disorder in a mammal, said method comprising: administering a foamable composition to said mammal, to treat said dermatological disorder, wherein said foamable composition comprises:
imiquimod in an amount from about 0.001% to about 10% by weight,
water in an amount from about 45% to about 90% by weight,
from 10% to 50% by weight of a $C_4$-$C_{24}$ fatty acid which is neutralized between 7.6% to 40% with a base,
an aerosol propellant,
and optionally an additional adjuvant selected from the group consisting of a complexing agent, a gelling agent, an antioxidant, a thickener, a preservative, a corrosion inhibitor, a penetration enhancer, colors fragrances, a pH adjusting agent and mixtures thereof, wherein all percentage values are based on the total weight of said foamable composition and wherein said foamable composition is contained in a pressurized container and produces a foam that breaks easily with shear when released from said pressurized container.

2. The method of claim 1, wherein said fatty acid is a $C_8$-$C_{18}$ fatty acid.

3. The method of claim 2, wherein said fatty acid is a $C_{18}$ fatty acid.

4. The method of claim 3, wherein said fatty acid is a member selected from the group consisting of stearic acid, isostearic acid, oleic acid, vaccenic acid, linoleic acid, alpha-linolenic acid, gamma-linolenic acid and eleostearic acid.

5. The method of claim 2, wherein said fatty acid is an iso-fatty acid.

6. The method of claim 2, wherein said fatty acid is capric acid.

7. The method of claim 1, wherein said fatty acid is neutralized between 20% to 40% with a base.

8. The method of claim 1, wherein said base is an amine, metal oxide, metal hydroxide, or the imiquimod.

9. The method of claim 8, wherein said base is triethanolamine.

10. The method of claim 1, further comprising a surfactant selected from the group consisting of a non-ionic surfactant, cationic surfactant, an anionic surfactant, a zwitterionic surfactant, an amphoteric surfactant, an ampholytic surfactant, and mixtures thereof.

11. The method of claim 10, wherein said surfactant is present in an amount up to about 50% by weight, based on the total weight of said foamable composition.

12. The method of claim 1, further comprising an emollient selected from the group consisting of an occlusive agent and a humectant.

13. The method of claim 12, wherein said emollient is an occlusive agent.

14. The method of claim 13, wherein said occlusive agent is selected from the group consisting of a mineral oil, grease, petrolatum, an animal fat, a vegetable fat, a water insoluble polymer, a fatty alcohol, and mixtures thereof.

15. The method of claim 13, wherein said occlusive agent is present in an amount of about 0.1% to about 10% by weight, based on the total weight of said foamable composition.

16. The method of claim 1, further comprising a buffering agent or a pH adjusting agent.

17. The method of claim 16, wherein the pH of said foamable composition is from about pH 4.0 to about pH 9.0.

18. The method of claim 1, wherein said aerosol propellant is selected from the group consisting of a hydrocarbon, a chlorofluorocarbon, dimethyl ether, hydrofluorocarbons, and mixtures thereof.

19. The method of claim 1, wherein said foam is homogenous.

20. The method of claim 1 wherein said dermatological disorder is actinic keratosis, basal cell carcinoma or external genital warts.

* * * * *